(12) United States Patent
Watanabe et al.

(10) Patent No.: US 12,357,012 B2
(45) Date of Patent: Jul. 15, 2025

(54) ANTI-ALLERGY FUNCTIONAL FOOD COMPOSITION, COSMETIC AND PERCUTANEOUS EXTERNAL AGENT

(71) Applicants: SOSIN CO., LTD., Tokyo (JP); Tomoki Fukuyama, Kanagawa (JP)

(72) Inventors: Itaru Watanabe, Tokyo (JP); Tomoki Fukuyama, Kanagawa (JP)

(73) Assignees: SOSIN CO., LTD., Tokyo (JP); Tomoki Fukuyama, Kanagawa (JP)

( * ) Notice: Subject to any disclaimer, the term of this patent is extended or adjusted under 35 U.S.C. 154(b) by 81 days.

(21) Appl. No.: 17/766,591

(22) PCT Filed: May 20, 2021

(86) PCT No.: PCT/JP2021/019105
§ 371 (c)(1),
(2) Date: Apr. 5, 2022

(87) PCT Pub. No.: WO2021/235512
PCT Pub. Date: Nov. 25, 2021

(65) Prior Publication Data
US 2024/0065305 A1    Feb. 29, 2024

(30) Foreign Application Priority Data
May 20, 2020    (JP) .................... 2020-087891

(51) Int. Cl.
*A23L 33/105* (2016.01)
*A23L 33/00* (2016.01)
*A61K 8/9789* (2017.01)

(52) U.S. Cl.
CPC ............. *A23L 33/105* (2016.08); *A23L 33/40* (2016.08); *A61K 8/9789* (2017.08); *A61K 2800/72* (2013.01)

(58) Field of Classification Search
CPC ..... A23L 33/105; A23L 33/40; A61K 8/9789; A61K 2800/72
USPC ........................................................ 426/655
See application file for complete search history.

(56) References Cited

FOREIGN PATENT DOCUMENTS

| | | | | |
|---|---|---|---|---|
| JP | 2001128643 A | * | 5/2001 | ............ A61K 36/22 |
| JP | 2003-221328 | | 8/2003 | |
| JP | 2012-97018 | | 5/2012 | |
| JP | 5967492 | | 8/2016 | |
| JP | 2017-75098 | | 4/2017 | |
| JP | 2018-83764 | | 5/2018 | |
| JP | 2019-43945 | | 3/2019 | |
| JP | 2020-62006 | | 4/2020 | |
| KR | 10-2014-0111230 | | 9/2014 | |

OTHER PUBLICATIONS

Translation of JP-2001128643-A (Year: 2001).*
International Search Report (ISR) issued Jul. 20, 2021 in International (PCT) Application No. PCT/JP2021/019105.
(Continued)

*Primary Examiner* — Brent T O'Hern
(74) *Attorney, Agent, or Firm* — Wenderoth, Lind & Ponack, L.L.P.

(57) ABSTRACT

The present invention relates to an anti-allergy functional food composition, a cosmetic, and a percutaneous external agent containing mastic oil as an active component.

7 Claims, 11 Drawing Sheets

(56) References Cited

OTHER PUBLICATIONS

Jianou Qiao et al., "Mastic Alleviates Allergic Inflammation in Asthmatic Model Mice by Inhibiting Recruitment of Eosinophils", American Journal of Respiratory Cell and Molecular Biology, vol. 45, No. 1, pp. 95-100, 2011, cited in ISR.
Risako Kishimoto et al., "Topical treatment of Mastic significantly ameliorates inflammatory and pruritic response in a mouse model of atopic dermatitis", Proceedings for the 94th Annual Meeting of the Japanese Pharmacological Society, No. 2-Y-G3-1, p. 1, text, Mar. 2021, cited in ISR.
Office Action issued Jan. 6, 2025 in Chinese Patent Application No. 202180005801.5, with English language translation.
Xiuqin Wang, "Allergic disease knowledge", Editorial Board of the Health Series, Jul. 1989, First ed., pp. 80-82, with English machine translation.
Xie Haizhou Xie Lan, "Concise Chinese Medicine Handbook", First Ed., Aug. 1993, p. 235, with English machine translation.
Yang Qide, "Traditional Chinese Medicine Identification Experimental Technology", Jan. 1990, First ed., p. 249, with English machine translation.

\* cited by examiner

[Fig.1]
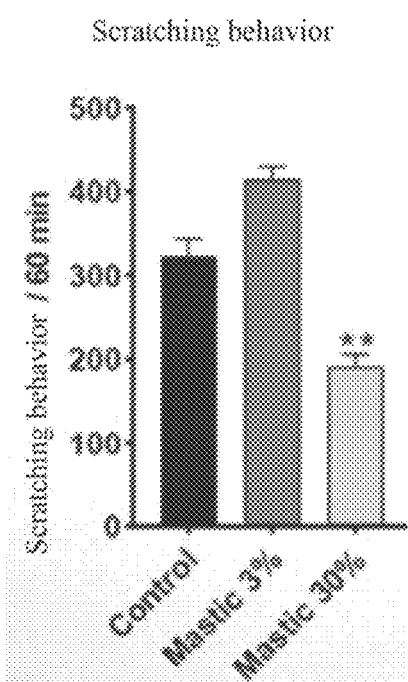
[Fig.2]
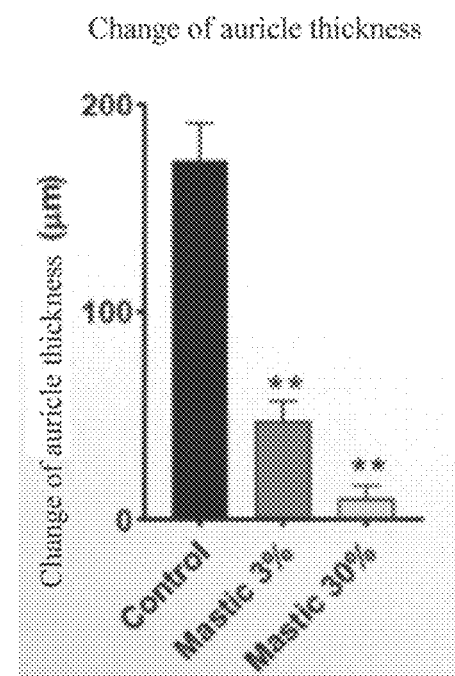

[Fig.3]
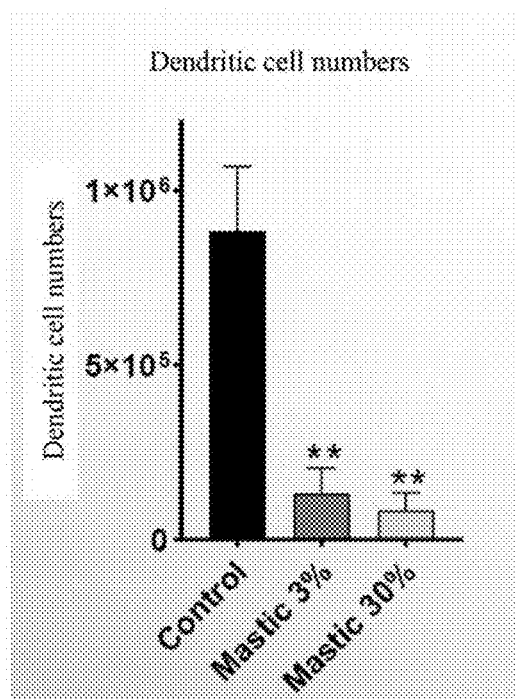
[Fig.4]
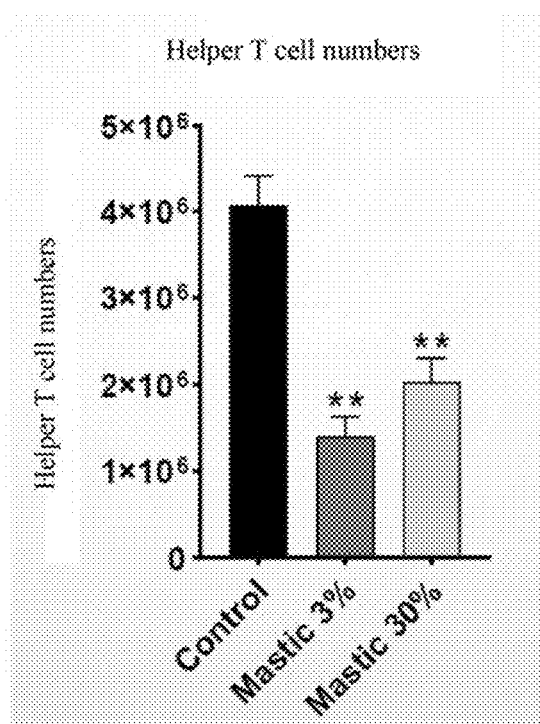
[Fig.5]
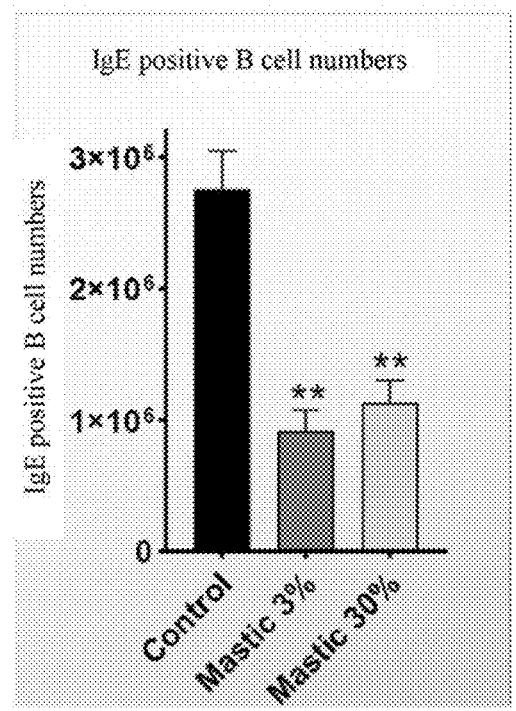

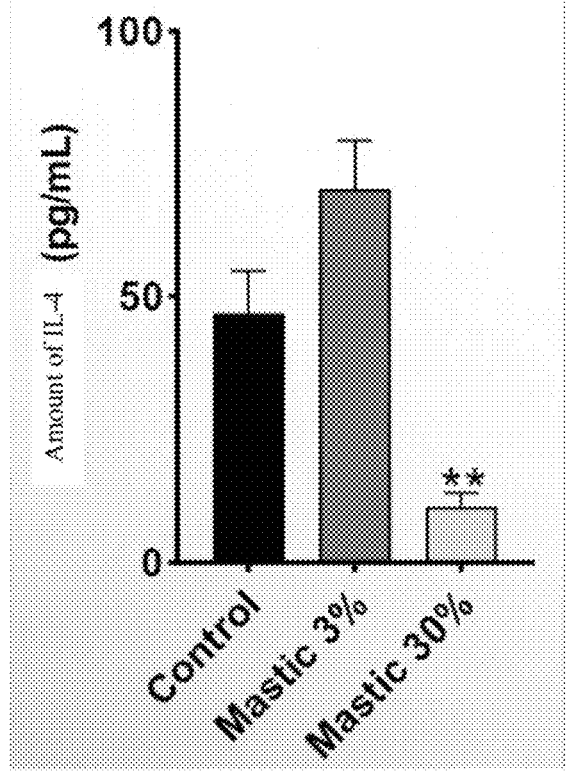
[Fig.6]
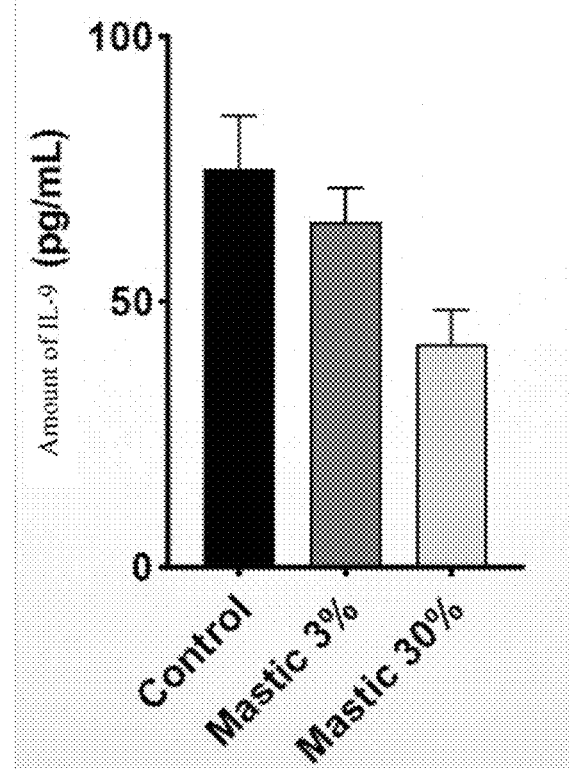
[Fig.7]
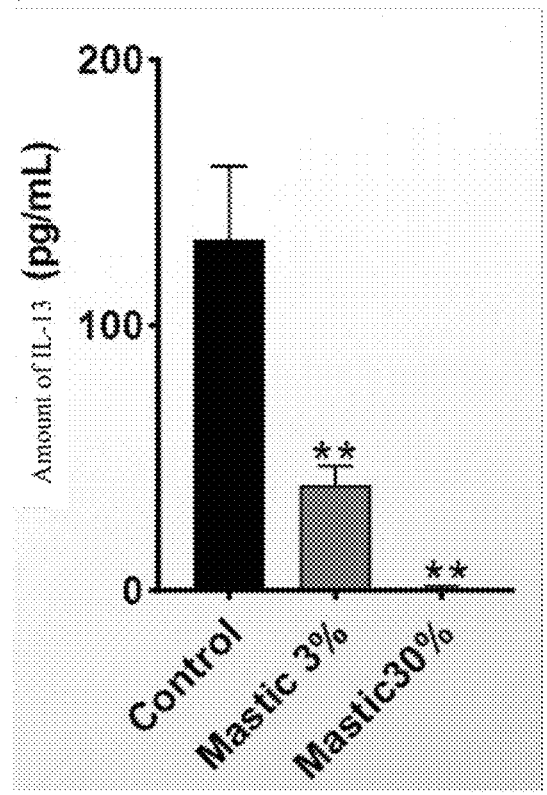
[Fig.8]

[Fig.9]
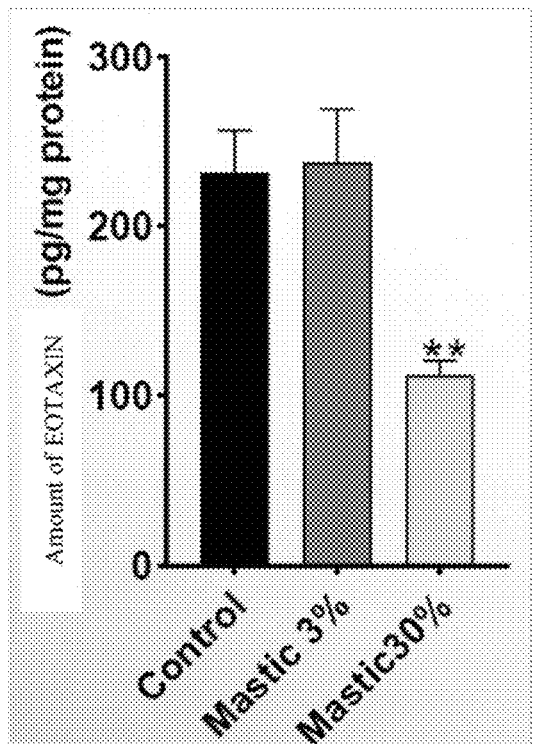
[Fig.10]
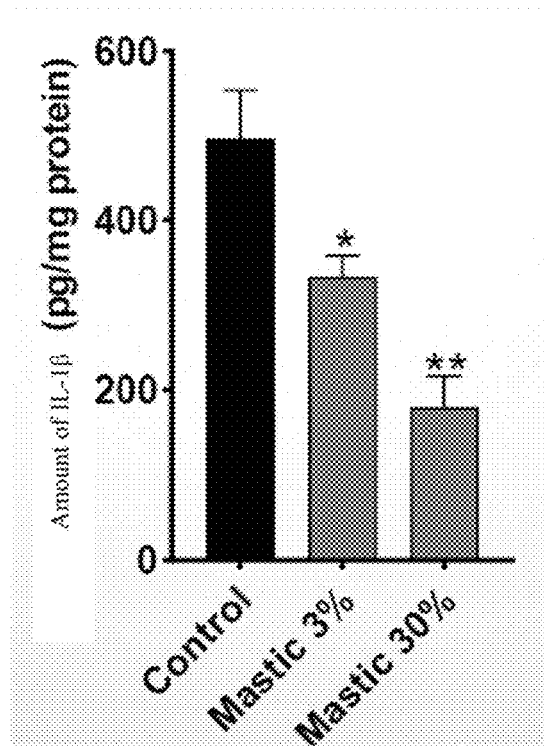
[Fig.11]
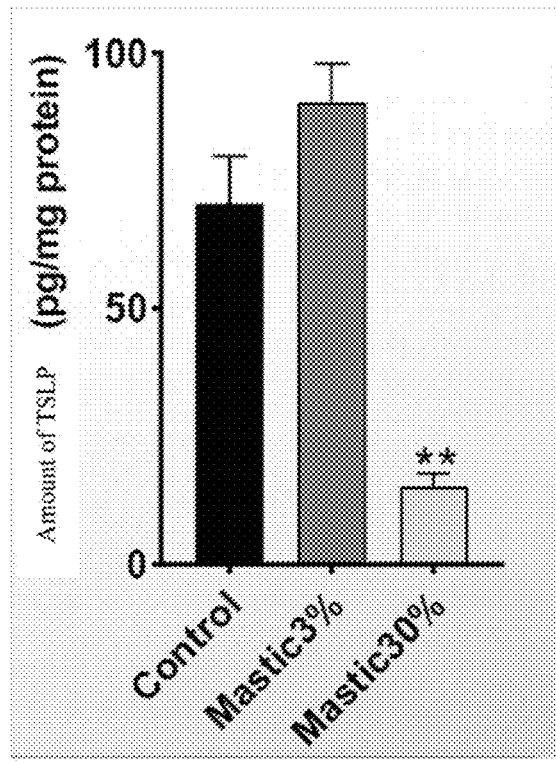

[Fig.12]
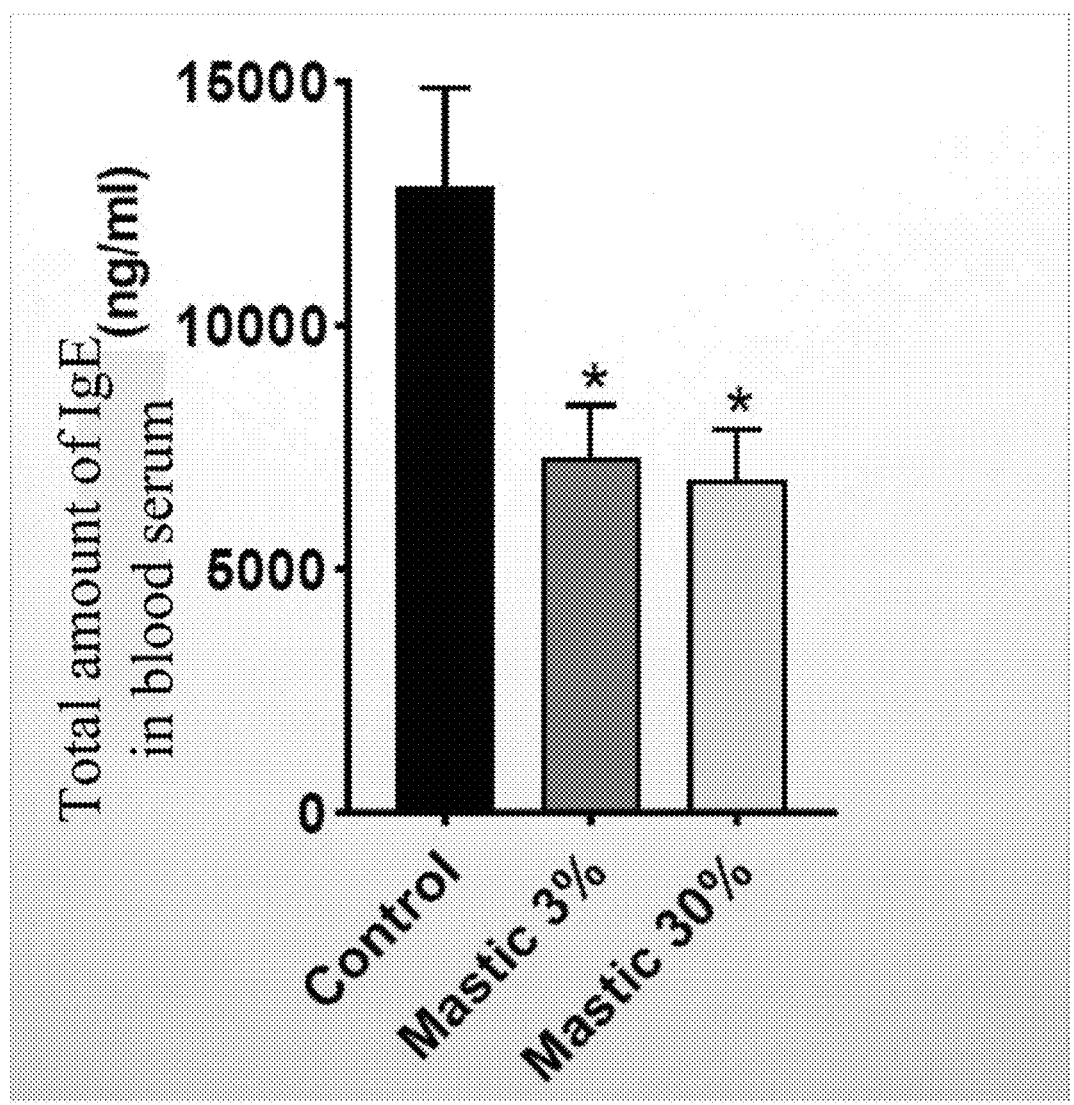

[Fig.13]
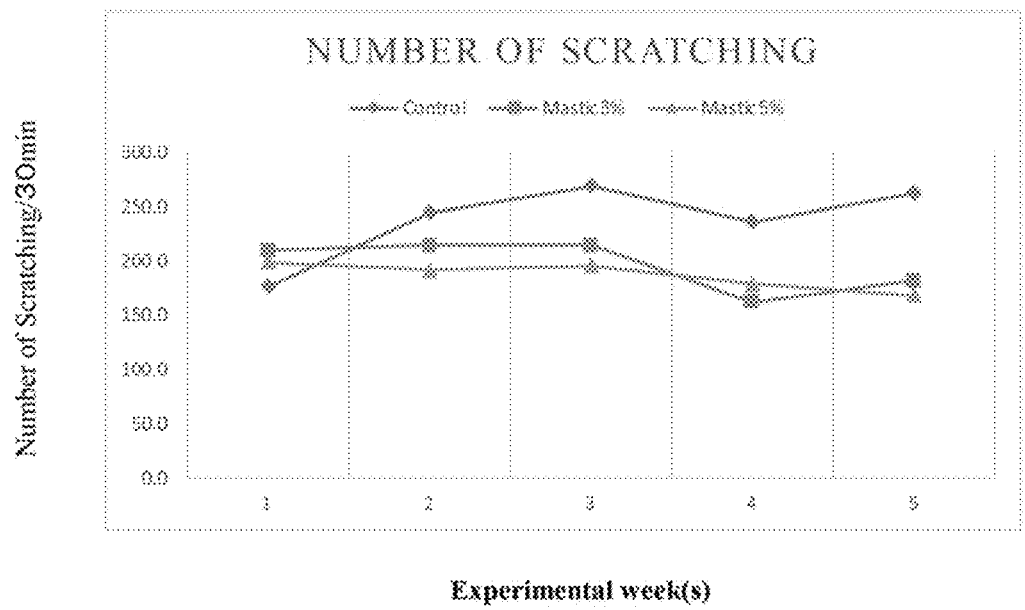
[Fig.14]
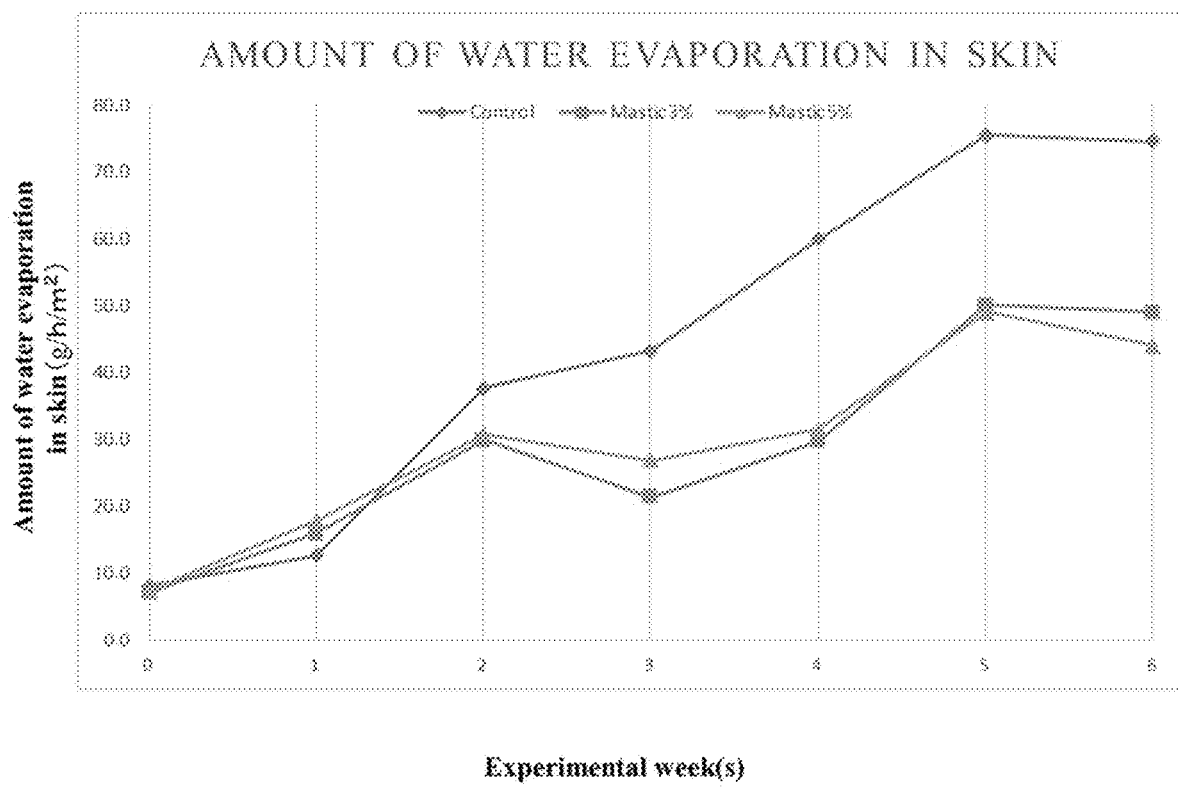

[Fig.15]
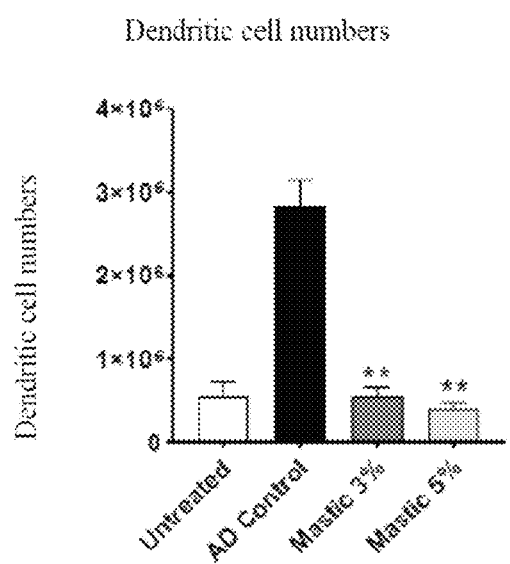
[Fig.16]
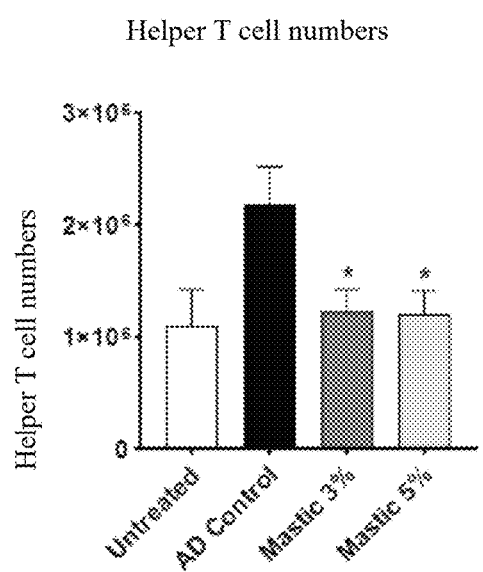
[Fig.17]
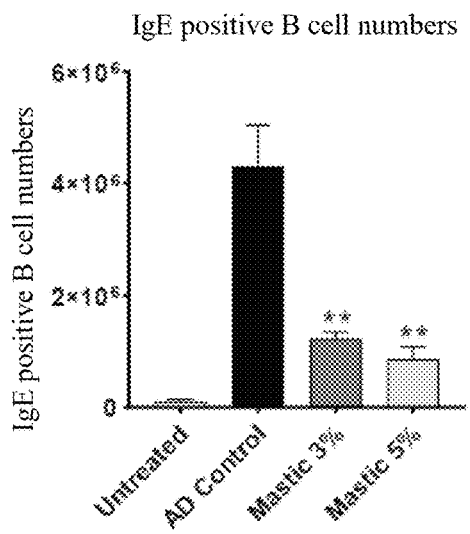

[Fig.18]
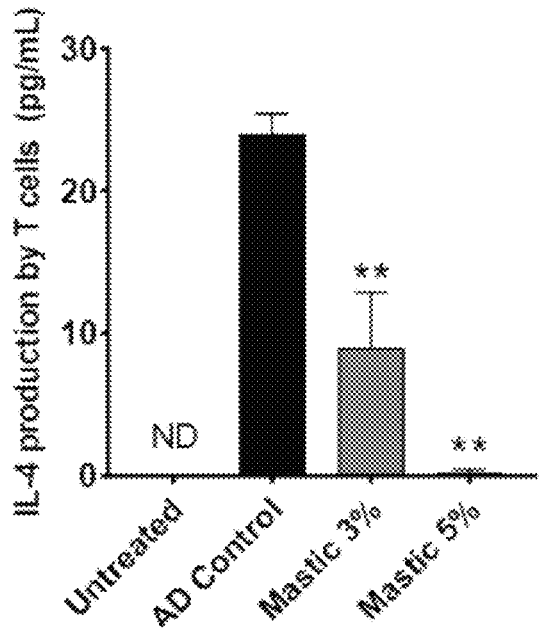
[Fig.19]
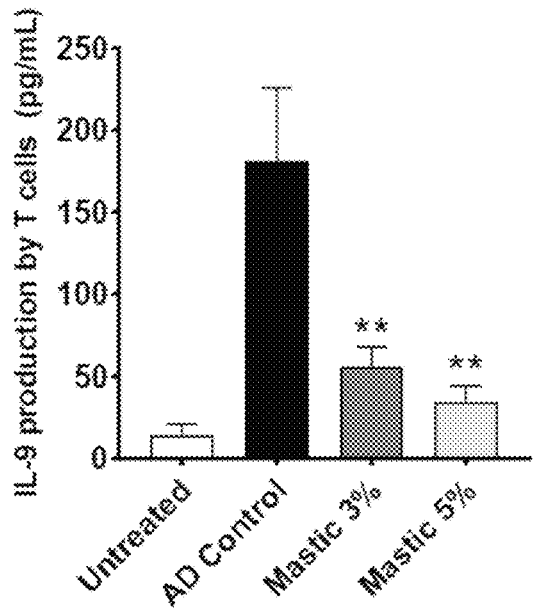
[Fig.20]
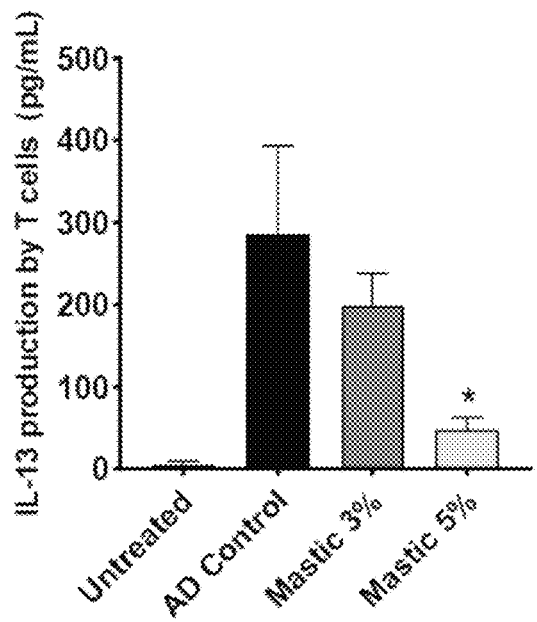

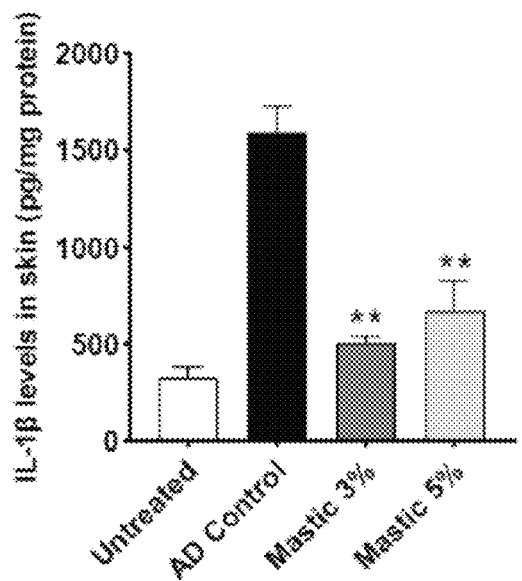
[Fig.21]
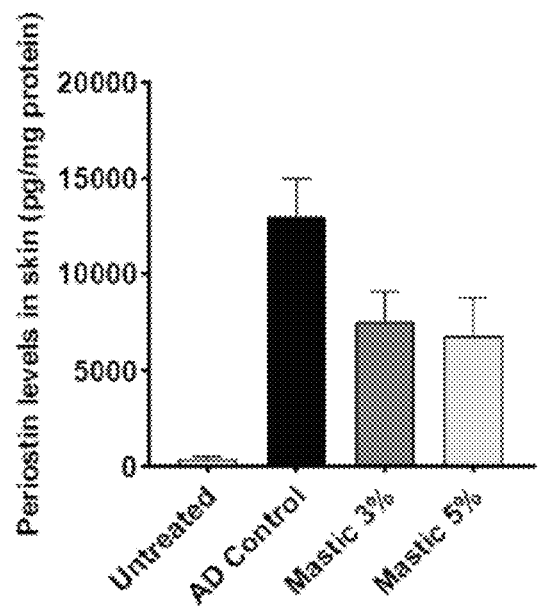
[Fig.22]
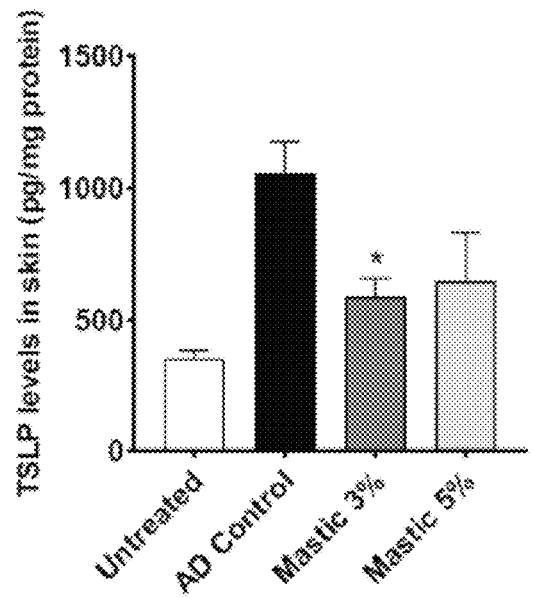
[Fig.23]

[Fig.24]
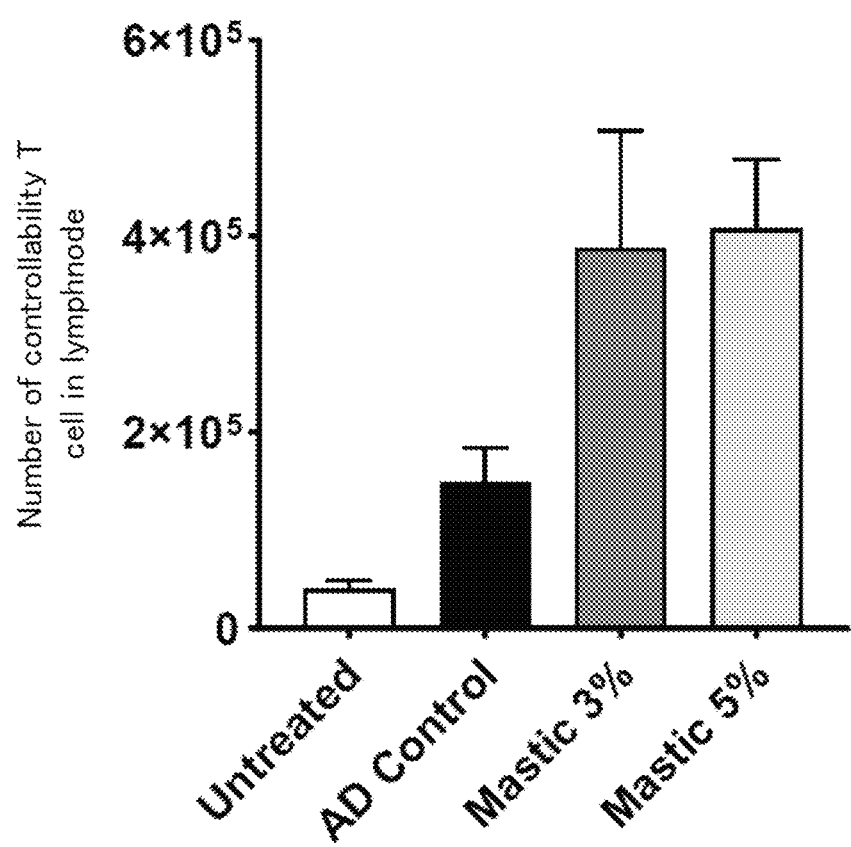

[Fig.25]
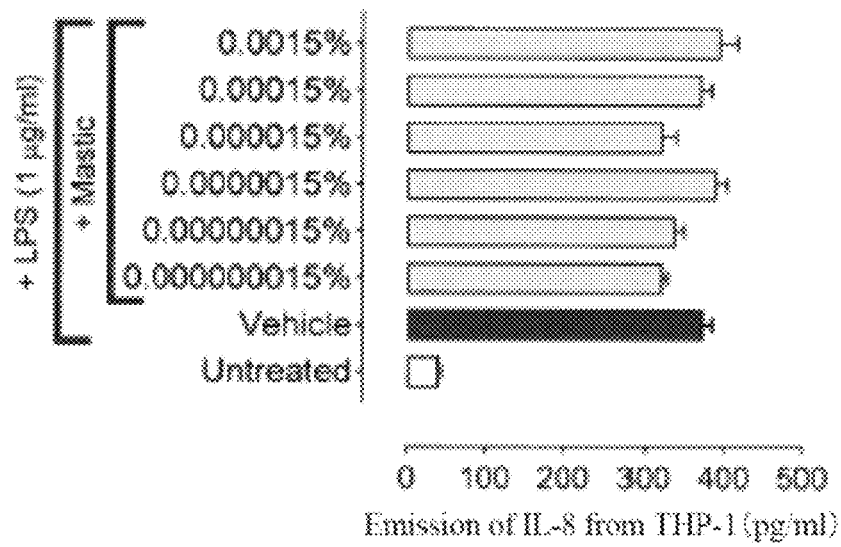
[Fig.26]
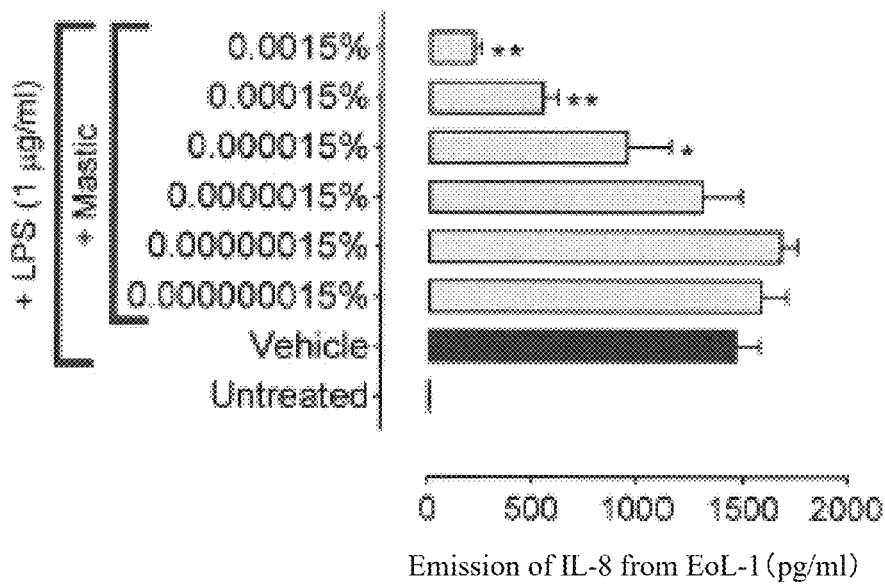

ANTI-ALLERGY FUNCTIONAL FOOD COMPOSITION, COSMETIC AND PERCUTANEOUS EXTERNAL AGENT

TECHNICAL FIELD

The present invention relates to an anti-allergy functional food composition, an anti-allergy cosmetic, and an anti-allergy percutaneous external agent containing mastic oil as an active component.

BACKGROUND ART

An allergy or an allergic reaction is so-called the reaction that an immunoreaction excessively reacts to a specific antigen. Although an allergenic cause is not explored, the cause is thought due to an excess explosion for the antigen, a generic inheritance, and so on in addition to a living environment. In addition, an antigen causing the allergy is especially called "allergen". The allergen is due to truly various things such as house dust, an object deriving from a living organism or a plant, e.g., hair of dog or cat, tick, mold, pollen and so on, an object deriving from a food, e.g., soba, rice, wheat, yeast, gelatin, dairy products, ovum gallinaceum and so on. Also, an agent is the allergen according to a component of the agent.

Here, the mechanisms of which the immunoreaction reacts to the allergen are an overreaction with regard to allergens of immunoglobulin strain anti bodies such as IgE, IgG or IgM, an overreaction with regard to an allergen of sensitized T cell, an overreaction with regard to allergens of helper T cell or its subspecies (e.g. Th1, Th2 cells) and/or heterophilic leucocyte, acidophilic leucocyte, macrophage, cytokine (mainly interleukin (IL)), and so on.

Then, such as allergic dermatitis, allergic rhinitis (pollinosis), allergic conjunctivitis, allergic gastroenteritis, bronchitic asthma, infantile asthma, food allergy, hypersensitivity, urticarial, and so on, i.e., allergic disease is caused by the allergy reaction. The allergic disease is mainly caused in man, however, the disease, such as dermatitis, conjunctivitis, and so on, is caused in other mammalians (e.g. dog or cat) as with man.

By the way, the agent treats the allergic disease, i.e., there are antagonist, inhibitor, retardant, or releaser with regard to receptors (e.g. leukotriene LT receptor or histamine $H_1$ receptor) or mediators (histamine or cytokine) themselves administering the extremely immunoreactions. In said antagonist, inhibitor, retardant, or releaser in the immunoreaction, they are roughly placed in a steroidal pharmaceutical preparation that steroid compound(s) is/are active component or a non-steroidal pharmaceutical preparation, for example, $1^{st}$ or $2^{nd}$ generation anti-histamine pharmaceutical preparation not depending on the steroid compound(s), chemical mediator releaser, and so on.

Generally, the steroidal pharmaceutical preparation mainly plays a role to reduce functions of the immunoreaction and the receptor or mediator administering the immunoreaction. Furthermore, the steroidal pharmaceutical preparation does not only play a role of the anti-allergy agent as an immune retardant but also uses as anti-inflammatory agent, vasoconstrictor, or cytostatic agent, and their dosage forms adopt every forms selected from internal medicine, percutaneous external agent (liniment), eye drop, drip infusion, and so on. However, if the steroidal pharmaceutical production is incorrectly used closer to mild or slight injury state or subclinical state, there is problem that it is more likely to accompany side actions because an inhibitory action is caused on an unrelated factor (e.g., hormone such as insulin and so on) to allergy or disease. Moreover, the non-steroidal pharmaceutical allergy agent represented by antihistamine agent also has the problem that it is more likely to accompany side actions as with the steroidal pharmaceutical production.

THE LIST OF PRIOR ART DOCUMENT

Patent Document

Patent Document 1: Japanese Patent Publication No. 2003-221328 A
Patent Document 2: Japanese Patent Publication No. 5967492 B
Patent Document 3: Japanese Patent Publication No. 2018-83764 A
Patent Document 4: Japanese Patent Publication No. 2017-75098 A
Patent Document 5: Japanese Patent Publication No. 2019-43945 A

SUMMARY OF THE INVENTION

Problems to be Solved by the Invention

To reduce the side effects of the anti-allergic agent in both the steroidal pharmaceutical preparation and/or the non-steroidal pharmaceutical preparation, for example, a skin sound agent using L-arginine and/or ethanolamine (provided amine is selected from any one of primary, secondary, or tertiary amine.) is described in Japanese Patent Publication No. 2003-221328 A (Patent Document 1). The agent described in Patent Document 1 retains active components and controls side effects by using L-arginine and/or ethanolamine. However, in the skin sound effect of the agent described in Patent Document 1, L-arginine and ethanolamine are only used for the purpose of controlling side effects, and a known medicine is only used as medicinal ingredients of immunosuppressive agent etc. Then, the examples of Patent Document 1 are only visually ascertainable degree tests such as anti-inflammatory action, anti-aging action and so on, there are concretely neither description nor suggestion how activating the receptor or mediator administering the immunoreaction.

Here, instead of the active components containing the general steroidal preparation and/or non-steroidal preparation, an immune retainer containing an agonist of protein is, e.g., described in Japanese Patent Publication No. 5967492 B (Patent document 2). In the retainer in Patent document 2, effects can be expected for an autoimmune disease, an immunological rejection after an organ transplantation, and a prevention and/or a treatment of the allergic disease or inflammatory disease by using the agonist of protein. Besides, the retainer in Patent document 2 has less side effect than the general steroidal preparation and/or non-steroidal preparation because it essentially consists of protein, in other words, it does not need auxiliaries for restraining the side effects like Patent document 1. However, with regard to the retainer in Patent document 2, an amino acid sequence for the agonist must be found, and the retainer cannot be prepared without a biological method, therefore, it is likely to high cost because it is not possible to prepare without a research facility of which arrangement is complete.

In case of using a synthetic chemical method used in the general steroidal preparation and/or non-steroidal preparation or using the biological method used in Patent document 2, there are concerned that they are cost, and that the side effects must be controlled by, e.g., the auxiliaries described in Patent document 1 if becoming clear how acting the receptor or mediator.

Then, in recent years, an immunoregulation composition regard to a natural product is, for example, described in Japanese Patent Publication No. 2018-83764 A (Patent Document 3). The composition in Patent Document 3 is the composition which expresses an immune function with Asteraceae *Cirsium maritimum* Makino or extract thereof as active component. Then, the composition is used by mixing in food and so on. However, in Patent Document 3, cirsimarin and/or cirsimaritin containing the *Cirsium maritimum* Makino extract is/are main components of the immunoregulation, and in Patent Document 3, there is description that the *Cirsium maritimum* Makino can be used on about whole plant parts thereof such as a leaf, a stem, and so on, though dry matters thereof is used by extracting with hot water as a result. To increase the more accuracy as the immunoregulation composition, cirsimarin and/or cirsimaritin must be isolated by further purifying the extract with chromatography and so on. Also, there is more possibility that the removal solvent burdens according to the solvent using.

The above organic solvent does not need to be used, for example, mastic (mastiha) etc. are known as materials that are able to be isolated and purified. Mastic (mastiha) indicates Anacardiaceae *Pistacia* Mastics (*Pistacia lentiscus*), and it produces in Hios in Greek only. Then, mastic is known about a sterilization or an anti-microbe effect, the action and effects, such as a sterilization for *Helicobacter pylori* or *Botulism bacillus*, a sterilization effect for periodontal disease bacteria regardless of man or animals other than man (e.g. dog, cat), a hypotensive action, a blood glucose level-lowing action, a cholesterol lowing action, an immunostimulation effect, an acceleration of a bile secretion, a prevention of a coating of tongue, alleviations of gout or rheumatism, a wound sterilization, a wound healing acceleration, and so on, are known in recent years. Generally, mastic is used by separating three types, which are "mastic sap" containing masticadienonic acid, isomasticadienonic acid, triterpenoid, aldehydes, alcohols, poly-β-myrcene, and so on, "mastic resin" naturally drying and solidifying the mastic sap, "mastic essential oil" essentially oiling volatile components (mainly terpenoid) by using steam distillation method or dry distillation for mastic sap or mastic resin. When separating mastic to said respective forms, it is possible to extract or isolate by convenient and safety methods, such as naturally drying, steam distillation, and so on, without organic solvents.

The applicants of the present application disclosure an oral composition containing mastic derived components for periodontal disease bacteria of dog or cat in Japanese Patent Publication No. 2017-75098 A (Patent Document 4). Here, in Patent Document 4, there are neither description nor suggestion with regard to an anti-allergic effect at which the present application aim and an effect of immunostimulation or immunosuppression. Then, an immunomodulator is described in Japanese Patent Publication No. 2019-43945 A (Patent Document 5). However, there are neither description nor suggestion that the modulator in Patent Document 5 gives some kind of effects such as suppression or activation with regard to the immunoreaction about mastic but entirely aims in essence, i.e., a relax effect.

It is an object of the present invention to provide an anti-allergy functional food composition, a cosmetic, and a percutaneous external agent containing mastic essential oil, as an active component, and mortifying a manufacturing cost by using the mastic component, especially mastic essential oil.

Means for Solving the Problems

In order to accomplish the present invention, an anti-allergy functional food composition, characterized by containing a mastic component as an immunosuppressive participating component.

Further, in order to accomplish the present invention, said mastic component is selected from any one of mastic powder, mastic oil, mastic essential oil, or mastic water, or wherein said mastic oil is made by solving diluent and is a solution of the diluent of which concentration is 0.1~60 weight %, or wherein said diluent is selected from any one of polyhydric alcohol fatty acid ester, alcohol solvent, mineral oil or vegetable oil, or wherein a blending amount of said mastic powder is 0.01~80% to said anti-allergy functional food composition, or wherein a blending amount of said mastic oil is 0.01~80% to said anti-allergy functional food composition, or wherein a blending amount of said mastic essential oil is 0.01~3% to said anti-allergy functional food composition, or wherein a blending amount of said mastic water is 0.1~100% to said anti-allergy functional food composition, or wherein a form of said anti-allergy functional food composition adopts the form of tablet, capsule, drop, gel, granule, powder or liquid, or wherein an immunosuppressive target allergy is I type or IV type in Coombs classification.

In order to accomplish the present invention, an anti-allergy cosmetic or an anti-allergy percutaneous external agent using the anti-allergy functional food composition.

Advantageous Effects of the Invention

According to the anti-allergy functional food composition of the present invention, it is clear to control the manufacture cost by using the mastic resin and/or the mastic essential oil and to show the immunosuppression of the mediators (cytokine, cytokinin), especially of man and dog and cat.

Further, it is possible to produce the food composition, the cosmetics, or the percutaneous external agent each having no side effects or few side effects because using the mastic components (especially oil).

BRIEF DESCRIPTION OF THE SEVERAL VIEWS OF THE DRAWINGS

In the accompanying drawings:

FIG. 1 is a graph showing a scratching behavior of an allergic dermatitis model mouse in EXAMPLE 1;

FIG. 2 is a graph showing an auricle thickness measurement result of the allergic dermatitis model mouse in EXAMPLE 1;

FIG. 3 is a graph showing a measurement result of dendritic cell numbers measured in EXAMPLE 1;

FIG. 4 is a graph showing a measurement result of helper T cell numbers measured in EXAMPLE 1;

FIG. 5 is a graph showing a measurement result of IgE positive B cell numbers measured in EXAMPLE 1;

FIG. 6 is a graph showing the amount of cytokine (IL-4) measured in EXAMPLE 1;

FIG. 7 is a graph showing the amount of cytokine (IL-9) measured in EXAMPLE 1;

FIG. 8 is a graph showing the amount of cytokine (IL-13) measured in EXAMPLE 1;

FIG. 9 is a graph showing the amount of EOTAXIN measured in EXAMPLE 1;

FIG. 10 is a graph showing the amount of IL-1β measured in EXAMPLE 1;

FIG. 11 is a graph showing the amount of TSLP (thymic stromal lymphopoietin) measured in EXAMPLE 1;

FIG. 12 is a diagram showing the amount of total IgE in blood serum (supernatant);

FIG. 13 is a graph showing a scratching behavior of an allergic dermatitis model mouse in EXAMPLE 2;

FIG. 14 is a graph showing the amount of water evaporation measured in EXAMPLE 2;

FIG. 15 is a graph showing a measurement result of dendritic cell numbers measured in EXAMPLE 2;

FIG. 16 is a graph showing a measurement result of helper T cell numbers measured in EXAMPLE 2;

FIG. 17 is a graph showing a measurement result of IgE positive B cell numbers measured in EXAMPLE 2;

FIG. 18 is a graph showing the amount of cytokine (IL-4) measured in EXAMPLE 2;

FIG. 19 is a graph showing the amount of cytokine (IL-9) measured in EXAMPLE 2;

FIG. 20 is a graph showing the amount of cytokine (IL-13) measured in EXAMPLE 2;

FIG. 21 is a graph showing the amount of IL-1β measured in EXAMPLE 2;

FIG. 22 is a graph showing the amount of Periostin measured in EXAMPLE 2;

FIG. 23 is a graph showing the amount of TSLP (thymic stromal lymphopoietin) measured in EXAMPLE 2;

FIG. 24 is a graph showing a measurement result of controllability T cell numbers in lymphnode measured in EXAMPLE 3;

FIG. 25 is a graph showing a suppression of an emission of IL-8 from man acute monocytic leukemia cell (THP-1) in EXAMPLE 3; and FIG. 26 is a graph showing a suppression of an emission of IL-8 from eosinophilic leukemia cell (EoL-1) in EXAMPLE 3.

MODE FOR CARRYING OUT THE INVENTION

Hereinafter, an anti-allergy functional food composition in the present invention will now be explained in more detail. In the present invention, "mastic sap" indicates a sap gathered from *Pistacia lentiscus* of the Anacardiaceae, and its main components are, as mentioned above the section of BACKGROUND ART, masticadienoic acid, isomasticadienoic acid, triterpene, aldehyde, alcohol, poly-β-myrcene, and so on. "mastic resin" indicates the resin naturally drying and solidifying the mastic sap. Solution solving the mastic sap and/or the mastic resin in diluent as stated below is filtrated, and the solution is so-called "mastic oil". "mastic essential oil" indicates an essential oil made from a volatility component (mainly terpene) with a steam or dry distillation of the mastic sap or the mastic resin. Further, "%" is entirely weight percent in case no special description.

Further, in the anti-allergy functional food composition, an anti-allergy cosmetic and an anti-allergy percutaneous external agent of the present invention, anti-allergic reactions are effective for four allergic reaction types that are I, II, III, and IV types divided into Gell-Coombs classification. Furthermore, out of said four allergic reaction types, it is effective for, e.g., types I and IV developing dermatitis. Then, as antibodies of two allergic reaction types which are types I and IV, it is effective for (has depression effect) IgE cell, histamine produced from helper T cell, and mediator such as ECF-A, leukotriene, PAF, lymphokine, IL (interleukin), IFN-γ, cytokine, cytokinin, and so on.

Next, the respective mastic components will be explained.

First, mastic powder will be explained. The mastic powder is one embodiment of an important component showing availability for IgE cell, histamine produced from helper T cell, and mediator such as ECF-A, leukotriene, PAF, lymphokine, IL (interleukin), IFN-γ, cytokine, cytokinin, and so on in the present invention. The mastic powder is used by naturally drying the mastic sap and/or the mastic resin as mentioned above. Further, the mastic sap and/or the mastic resin is/are levigated, so the mastic sap and mastic resin have contained components hardly changing except for water is evaporated and they should be finally powder. Incidentally, with regard to the powder, it is possible to take a general method (e.g., mil, freeze drying, and so on) and take an arbitrary means in state of the mastic sap or the mastic resin.

A blending amount of the mastic powder can show the availability for the anti-allergy functional food composition of the present invention, in 0.01%~80%, in preferably 0.1~50%. If the blending amount of the mastic powder is less than 0.01%, an active effect is not shown for IgE cell, histamine produced from helper T cell, and mediator such as ECF-A, leukotriene, PAF, lymphokine, IL (interleukin), IFN-γ, cytokine, cytokinin, and so on. Moreover, if the blending amount of the mastic powder is more than 80%, there is concern that some inflammations or allergy reactions are rather caused, and, in some cases, there are possibilities that immunosuppressive effects are reduced for IgE cell, histamine produced from helper T cell, and mediator such as ECF-A, leukotriene, PAF, lymphokine, IL (interleukin), IFN-γ, cytokine, cytokinin, and so on within the concentration range. Moreover, if the blending amount of the mastic powder is more than 80%, there is a possibility to destroy antibodies etc. necessary in the body.

Incidentally, in the anti-allergy functional food composition of the present invention, according to the food embodiment, there is more convenient for combining by oil, i.e., as mastic oil than for combining solid powder like mastic powder. Here, the mastic oil will be explained. The mastic sap (resin) is used by solving in solvent as above. The reason for solving the resin in solvent is that the mastic sap (resin) itself is not solved in water and is the result of considering a compatibility with various additive agent when the composition adopts various dosage forms, such as gel, liquid and so on.

As diluent for solving the mastic sap (resin), it is possible to use polyhydric alcohol fatty acid ester such as glycerin, di-propylene glycol, 1,3-butylene glycol, fatty acid tri glyceride (fatty acid part is about 8~18 carbon numbers, preferably 8~12 carbon numbers above all), tri(caprylic acid/capric acid) glyceryl, fatty acid mono glyceride (fatty acid part is about 8~18 carbon numbers, preferably 8~12 carbon numbers above all), monocarpic glyceride, fatty acid ester (fatty acid part is about 8~18 carbon numbers, preferably 8~12 carbon numbers above all), isopropyl myristate, iso-octanoic acid ethyl ester, octyl dodecyl myristate, higher alcohol (about 8~22 carbon numbers), oleyl alcohol, sorbitan fatty acid ester (fatty acid part is about 8~18 carbon numbers, preferably 8~12 carbon numbers above all), sucrose fatty acid ester (fatty acid part is about 8~18 carbon numbers, preferably 8~12 carbon numbers above all), and/or natural fats, especially plant origin unsaturated fatty acid such as olive oil, coconut oil, and so on, saturated fatty acid such as palm oil and so on, plant or animal oil such as rape seed oil, cotton seed oil, sunflower oil, perilla oil, linseed oil, fish oil, soybean oil and corn oil, and alcohol solvent (provided, ethanol is used in case food, and ethanol or isopropanol is used in cosmetic or percutaneous external agent).

Further, the concentration of the mastic oil is preferably 0.1~60% solution of above diluent. By the way, if the concentration is 0.1% or below, the immunosuppressive effect is decreased or is not obtained for IgE cell, histamine produced from helper T cell, and mediator such as ECF-A, leukotriene, PAF, lymphokine, IL (interleukin), IFN-γ, cytokine, cytokinin, and so on. If the concentration is more than 60%, the mastic oil is heterogeneous solution and also decreases the immunosuppressive effect to the above mediator not so much as the concentration is below 0.1%.

A preparation method of the mastic oil should be routine method if following above concentration range. Then, the solution temperature of the mastic sap (resin) may increase the temperature if considering the boiling point of the solvent and may be in the ordinary temperature in some cases. Furthermore, it is preferable to use as the mastic oil after solving the mastic sap (resin) to the solvent with filtrating it.

Further, a blending amount of the mastic oil is 0.01~80%, preferably 0.1~80% to the total amount of the anti-allergy food functional composition of the present invention. The immunosuppressive effect is not enough shown if the blending amount of the mastic oil is 0.01% or below. Further, if the blending amount of the mastic oil is more than 80%, there is concern that some kind of an inflammation or allergic reaction are caused, and there is also possibility that an immunostimulation effect is rather increased lower than the concentration range of the mastic oil depending on the situation.

Next, mastic essential oil will be explained. By the way, as mentioned above, the mastic essential oil should use the oil which refines a volatility component (mainly terpene) by the steam distillation and dry distillation of the mastic sap or resin. Further, refining the volatility component should be routine procedure.

A blending amount of the mastic essential oil is 0.01~4%, preferably 0.01~3% to the anti-allergy food functional composition of the present invention thereby demonstrating its availability. If the blending amount of the mastic essential oil is more than 4%, as with the mastic oil, there is concern that some kind of an inflammation or allergic reaction are caused, and there is also possibility that the depression effect is reduced for IgE cell, histamine produced from helper T cell, and the mediator such as ECF-A, leukotriene, PAF, lymphokine, IL (interleukin), IFN-γ, cytokine, cytokinin, and so on depending on the situation. By the way, although the mastic essential oil shows the depression effect to the mediator such as ECF-A, leukotriene, PAF, lymphokine, IL (interleukin), IFN-γ, cytokine, cytokinin, and so on, even if the essential oil is not contained in the anti-allergy food functional composition of the present invention, that is, the mastic powder or oil only contains, the better depression effect is also obtained.

Next, mastic water will be explained. By the way, as mentioned above, the mastic water should use the water component which is separated by a steam distillation of the mastic sap or resin.

Further, a blending amount of the mastic water is 0.1~100%, preferably 1~50% to the anti-allergy food functional composition of the present invention thereby demonstrating its availability. If the blending amount of the mastic essential water is less than 0.1%, there is concern that the immunosuppressive effect is rather reduced or is not shown. Moreover, if the blending amount of the mastic essential oil is more than 100%, there is concern that some kind of the inflammation or allergic reaction are caused, there is possibility that the depression effect is reduced for these mediators in comparison of this concentration range, and there is possibility that the immunostimulation effect is rather increased.

Moreover, the anti-allergy functional food composition can adopt a type of tablet, capsule, drop, gel (jerry) type, granule, powder or liquid as a food type. More specifically, the composition can adopt an aspect of seasonings such as sauce, salad dressing and so on, confectioneries such as cookies, biscuits, cakes, chocolates, candy, tablet type refreshing candy and so on, nutritious supplements, dog and cat foods, beverages such as additive type (portion type e.g., granule, powder, condensation liquid), condensation type, or straight type (refreshing beverage). Further, in these food aspects, the mastic components may be added in production or after production with each general method. Also, the anti-allergy functional food composition of the present invention can be applied to cosmetic and/or percutaneous external agent.

Then, the anti-allergy functional food composition of the present invention can be selected any one of the mastic powder, the mastic oil, the mastic essential oil, or the mastic water. Furthermore, the anti-allergy functional food composition of the present invention may be also selected from two or more types of the mastic powder, the mastic oil, the mastic essential oil, or the mastic water.

As the above aspects, the anti-allergy functional food composition of the present invention can be archived, however, the composition may contain various additive agent.

Then, the anti-allergy functional food composition of the present invention is archived by containing *Lactobacillus* and lactic acid bacteria producing material as active component improving the immunosuppressive effect of the mastic components. Further, the length of *Lactobacillus* is not limited in this case.

The *Lactobacillus* or *Lactobacillus bifidus* using for the anti-allergy functional food composition of the present invention is *Lactobacillus* such as *Lactobacillus brevis*(*L. brevis*), *Lactobacillus brevis* subspecies *coagulans* (*L. brevis* subspecies *coagulans*), *Lactobacillus acidphilus* (*L. acidphilus*), *Lactobacillus gasseri* (*L. gasseri*), *Lactobacillus mali* (*L. mali*), *Lactobacillus plantarum*(*L. plantarum*), *Lactobacillus buchneri*(*L. buchneri*), *Lactobacillus casei* (*L. casei*), *Lactobacillus johnsonii* (*L. johnsonii*), *Lactobacillus gallinarum* (*L. gallinarum*), *Lactobacillus amylovorus* (*L. amylovorus*), *Lactobacillus rhamnosus* (*L. rhamnosus*), *Lactobacillus kefir* (*L. kefir*), *Lactobacillus paracasei*(*L. paracasei*), *Lactobacillus crispatus* (*L. crispatus*), *Lactobacillus lactis* (*L. lactis*), and so on, *Enterococcus* bacteria such as *Enterococcus faecalis*, *Enterococcus faecium* and so on, and *Bifidobacterium* bacteria such as *Bifidobacterium bifidum*, *Bifidobacterium longum* (*B. longum*), *Bifidobacterium adolescentis* (*B. adolescentis*), *Bifidobacterium infantis* (*B. infantis*), *Bifidobacterium breve* (*B. breve*), *Bifidobacterium catenulatum* (*B. catenulatum*), and so on. Further, it is preferable for the *Lactobacillus* or *Lactobacillus bifidus* concerned to use *Bacillus* mort. For the reason, it is easy for the *Bacillus* mort to prepare when using as the *Lactobacillus* of the present invention, and the *Bacillus* mort also substantially shows the immunosuppressive effect. Further, bacterial strains of these bacteria are no limitation. Moreover, as the lactic acid bacteria producing material, it is possible to use *Lactobacillus* lysate (e.g., derived products of *Lactobacillus crispatus*, that is, product name: KT-11HKN, KT-11 HP and so on) or *Lactobacillus* fermented extract (e.g., equol

*Lactobacillus*, reducing fermented *Lactobacillus*). Further, as *Lactobacillus* other than the above, it is also possible to use BLIS bacterium (*Streptococcus salivarius* K12 and M18), *Streptococcus thermophilus, Streptococcus xylosus, Streptococcus carnosus, Pediococcus pentosaceus, Leuconostoc mesenteroides*, or *Oenococcus oeni*, and both live bacterium and killed bacterium are acceptable about them.

Further, as for said *Lactobacillus*, it is preferable to incorporate 0.01-1.0% for the whole quantity of the anti-allergy functional food composition of the present invention. If the *Lactobacillus* is less than 0.01%, the immunosuppressive effect is not shown. Further, if the *Lactobacillus* is more than 1.0%, the immunostimulation effect may be shown on the contrary although the immunosuppressive effect is not shown.

Further, as the additive agent similar to the *Lactobacillus*, the anti-allergy functional food composition is made by further blending papaya extract and/or chitosan.

The papaya extract is an extract derived from a natural papaya fruit and the extract which is extracted by grinding the natural papaya fruit and soaking it in solvent such as ethanol and so on. The papaya fruit should be ripe one or unripe one which is still green. Although the blending amount of the papaya extract is particularly no restriction, the blending amount is preferably 0.005%-10% to the total amount of the anti-allergy functional food composition of the present invention. The above effect is not shown if less than 0.005%, and it has the possibility that immunosuppressive effect of anti-allergy functional food composition of the present invention can be contrarily increased if excessively more than 10%.

In contrast, chitosan is obtained by boiling and processing chitin obtained from an external skeleton of crustaceans, such as crab, shrimp and so on, with using strong base. Because chitosan is polysaccharide, it is used as adhesive. Although the blending amount of the chitosan is particularly no limited, the blending amount is preferably 0.005~10% to the total oral composition of the present invention. The above effect is not shown if less than 0.005%, and it has the possibility that immunosuppressive effect of anti-allergy functional food composition of the present invention can be contrarily increased if excessively more than 10%.

Furthermore, chitosan and papaya extract also should be formulated at the same time. Although the blending amount of chitosan and the papaya extract is particularly no limited, the blending amount is preferably 0.005~10% to the whole anti-allergy functional food composition of the present invention. The above effect is not shown if less than 0.005%, and it has the possibility that immunosuppressive effect of anti-allergy functional food composition of the present invention can be contrarily increased if excessively more than 10%.

Further, in the anti-allergy functional food composition of the present invention, as auxiliary enhancing the immunosuppressive effect of the mastic components in addition to chitosan and/or the papaya extract, i.e., enhancing a multiplier effect of the immunosuppressive effect, it is possible to blend egg-yolk oil, lysine ($\alpha$-amino acid), tannin derived from persimmon, natural extract containing polyphenol, lactoferrin, fat-soluble vitamin such as vitamin A, vitamin D, vitamin E and/or vitamin K, water-soluble vitamin such as vitamin C and vitamin B family containing folic acid, coenzyme family such as biotin, co-enzyme Q10 (ubiquinone) and so on, and carotenoid family such as lutein, astaxanthin, $\beta$-carotene.

Egg-yolk oil will be explained. With regard to the egg-yolk oil, between a solidification component or an oil and fat component produced by heating egg-yolk, the oil and fat component is generally called egg-yolk oil or egg oil. The general egg-yolk oil contains vitamin E (tocopherol) which is fat-soluble vitamin, egg-yolk lecithin, choline (phosphatidylcholine), phosphatidylethanolamine, fatty acid which are palmitic acid (carbon number=16, degree of unsaturation=0), stearic acid (carbon number=18, degree of unsaturation=0), oleic acid (carbon number=18, degree of unsaturation=1), and linoleic acid (carbon number=18, degree of unsaturation=2), phosphatide derived from said fatty acids, triglyceride, and so on. Further, although these components slightly change in component ratio with conditions such as kinds of chickens, feedstuff for chicken, sperm or unfertilized egg, rearing environment and so on, the components themselves do not change regardress of such components.

When using the egg-yolk oil in the present invention, there no limitations such as a preparation method of the egg-yolk oil, the difference of the rearing environment such as the feedstuff, farm and so on, or the sperm or unfertilized egg. Moreover, in the present invention, both using of commercial product and prior preparation are acceptable. Furthermore, in case of the prior preparation, the preparation method is general technique, and the conditions (e.g., heating temperature, material of container, and so on) of the method are no restriction. Moreover, in the anti-allergy functional food composition of the present invention, the egg-yolk oil, which is produced from egg having antibody by the mediator of the suppressive target and so on, however, there is no restriction, and the antibody is no limitation. Even, the antibody of egg is general method.

In the present invention, the egg-yolk oil is preferable to 1~30% for the anti-allergy functional food composition of the present invention. If less than 1%, the immunosuppressive effect is not enough able to be shown. If more than 30%, the immunosuppressive effect is not particularly shown, or it is possible to rather stimulate the mediator of the immunosuppressive effect.

Next, lysine will be explained. In case using lysine in the present invention, it is preferable to 0.005%-40% for the anti-allergy functional food composition of the present invention. If less than 0.005%, the immunosuppressive effect is not enough able to be shown. If more than 40%, the immunosuppressive effect is not particularly shown, or the immunostimulation effect may be conversely shown. The lysine using in the anti-allergy functional food composition of the present invention can be selected from anyone of $\alpha$-L-lysine, $\alpha$-L-lysine monohydrochloride salt, or $\varepsilon$-poly (L-lysine).

Next, in case of using a natural product containing poly phenol, it is selected from any one of flavonoid, catechin or tannin phenols such as indigo plant extract, tea plant (green tea, oolong tea, black tea) extract, sweet tea extract, powdered tea, cherry leaf extract, lemon extract, white birch extract, grape, apple, blueberry, raspberry, chocolate, cocoa, soybean, loquat extract, burnet extract, *Hypericum erectum* extract, *Hamamelis* extract, *Scutellaria* root extract, wild rose extract, perilla seed extract, guava leaf extract, grape seed extract, wine extract, grape leaf extract, apple extract, apple tannin, and so on, and the indigo plant extract, the tea (green tea) extract, the cherry leaf extract, and the lemon extract are preferable as the immunosuppressive effect can be especially expected.

Incidentally, the natural product extract containing poly phenol using in the present invention is preferable to 0.01~40% for the anti-allergy functional food composition of the present invention similar to lysine. If less than 0.01%, the immunosuppressive effect is not enough able to be shown. If more than 40%, the immunosuppressive effect is not particularly shown, or the immunostimulation effect may be conversely shown. Further, the natural product extract containing poly phenol is generally put on market as a solution of an extract solvent (e.g., alcohol, water) of the extract. If a concentration control of the extract solution is necessary, alcohol or water itself should be use for dilution.

Next, general food additive(s) may be added to the anti-allergy functional food product, the cosmetic and the percutaneous external agent of the present invention.

The inorganic additive(s) is/are selected from dibasic calcium phosphate dihydrate, dibasic calcium phosphate anhydrate, calcium pyrophospahte, tribasic magnesium phosphate, tribasic calcium phosphate, aluminium hydroxylate, alumina, light calcium carbonate, heavy calcium carbonate, magnesium carbonate, and so on. It is possible to simultaneously use one kind of them or more than two kinds of them. The amounts of these inorganic additives are generally 0.001~20% to the anti-allergy functional food composition of the present invention.

The humectant(s) is/are selected from polyvalence alcohol such as glycerin, conc.glycerin, diglycerin, sorbit multitol, dipropylene glycol, propylene glycol, 1,3-butylene glycol, xylitol, polyethylene glycol and so on, plant extract such as rosemary extract, Sasa albo-marginata extract, *Chrysanthemum* extract, and so on, polysaccharide such as sorbit liquid, and whey derived from milk, and one kind of them or two kinds of them can be used.

The binder(s) (thickener(s)) is/are selected from carrageenan, alginic acid and the derivative such as sodium alginate, alginic acid propylene glycol ester, sodium alginate containing calcium, potassium alginate, calcium alginate, ammonium alginate and so on, xanthan gum, gum guaiac, gelatin, agar, sodium carboxymethylcellulose, hydroxyethylcellulose, hydroxypropylcellulose, sodium poly acrylate, pullulan and natural oil and fats such as coconut oil, palm oil, rape seed oil, cotton seed oil, sunflower oil, perilla oil, linseed oil, soybean oil, fish oil, glycerin fatty acid ester and so on, and it is possible to use one kind of them or more than two kinds of them.

The preservative(s) or antiseptic(s) is/are selected from sodium benzoate, sorbic acid or potassium sorbate, stabilized type chlorine dioxide, hinokithiol, grape fruit seed extract, natural aroma oil and essential oil such as clove oil, peppermint pol and so on, and it is possible to use one kind of them or more than two kinds of them.

The pH (hydrogen ion concentration) modifier is selected from citric acid, (mono- or di-) sodium citrate, malic acid, (mono- or di-) sodium malate, gluconic acid, (mono- or di-) sodium gluconate, succinic acid, sodium succinate, lactic acid, (mono- or di-) sodium lactate, potassium carbonate, sodium hydrogen carbonate, and so on, it is possible to use one kind of them or more than two kinds of them.

As the retention agent for retaining the active component in the anti-allergy functional food composition of the present invention, it is possible to use selected from liquid paraffin, gelatinized hydrocarbon which is a mixture of liquid paraffin and polyethylene, vegetable oil, yellow bees wax, and so on and combined use one kind of them or more than two kinds of them. Further, said gelatinized hydrocarbon also plays a role as gelatinizer.

The sweetener is sodium saccharin, aspartame, L-phenyl alanine compound, trehalose, stevioside, stevia extract, p-methoxy cynnamaldehyde, neohesperidin dihydrochalcone, periraltin, xylitol, sorbitol, erythritol, honey, oligosaccharide, dextrin, and so on. Further, the sugar alcohol such as xylitol, sorbitol, erythritol, and so on plays a role as the immunosuppressive effect auxiliary.

As the aroma chemical component, it is possible to combined use one kind or more than two kinds of the components selected from 1-menthol, anethole, menthon, cineol, limonene, carvone, methyl salicylate, ethyl butyrate, eugenol, thymol, cinnamaldehyde, trans-2-hexenal, and so on. These components should combine separately, however, essential oil containing said components should be used.

By the way, although the blending amount of the respective components as mentioned above humectant, binder, retention agent, sweetener, preserve, aroma chemical component, and so on, is no limited, the blending amount is generally 0.001~20% to the whole anti-allergy functional food composition.

Further, fatty alcohol or ester thereof, terpenoid hydrocarbon or terpenoid alcohol, phenol ether, aldehyde, ketone, an aroma component such as lactone and so on, essential oil should be mixed at the range not obstructing the effect of the present invention in addition to said aroma chemical component. The blending amount of the aroma component is generally 0.001~20% to the whole anti-allergy functional food composition.

In the anti-allergy functional food composition of the present invention, other further effective component should be mixed. Such component(s) is/are selected from ascorbic acid (vitamin C), ascorbic acid salt derivative, tocopherol, sodium chloride, dextranase, and so on, and it is possible to mix one kind of them or more than two kinds of them. The blending amount of the effective component is generally 0.001~20% to the anti-allergy functional food composition.

Then, in case mixing the above mastic resin (however as mastic resin solution), the mastic essential oil, the egg-yolk oil, additive etc. on the above range toward the whole anti-allergy functional food composition of the present invention, the residue should be used as solvent (e.g. the solvent for solving the mastic resin), gelatinizer, and so on.

The anti-allergy functional food composition of the present invention can prepare in proportion to the general method, and the method is no particularly limited. Moreover, the cosmetic and percutaneous external agent of the present invention can also prepare based on the above additives and so on and is also in proportion to the general method.

As presented above, the anti-allergy functional food composition in the present invention are explained, the embodiments of the present invention are no limited.

EXAMPLES

Test (Examples) are further explained to confirm above embodiments of the anti-allergy functional food composition in the present invention.

[Example 1] Oral Administration Test of the Mastic Oil for Hapten Derivative Allergic Dermatitis Model Mice In the Example 1, to test the effect of the mastic oil for Th2 type reaction generated from Th2 cell which is subgroup of helper T cell inducing allergic dermatitis, the oral administration test was accomplished by using the hapten derivative allergic dermatitis model mouse.

First, the hapten derivative allergic dermatitis mouse (hereinafter, "allergic dermatitis model mouse(s)") used BALB/c SPF mouse (hereinafter, simply called "mouse") produced by Japan SLC Co, LtD. The allergic dermatitis model mouse was prepared by administering trilene-2,4-diisocyanate (TDI) as the hapten several times after domesticating the mouse on ten days receiving later. Further, abdominal hair of the mouse was removed before the day of first administration of TDI, moreover, TDI was administered on abdomen of the mouse again after removing the abdominal hair in three weeks from the first administration (sensitization). Furthermore, an elicitation of the mouse was caused by administering TDI to auricular region and dorsocervical of the mouse respectively in one week from the sensitization again.

Here, with regard to the administration of the mastic oil for the allergic dermatitis model mouse, the oil solving in corn oil was orally administered in about five weeks contiguously from the domestication start after the mouse arriving to the elicitation by administering TDI to auricular region and dorsocervical of the mouse respectively. Further, with regard to the allergic dermatitis model mice, three mice which are a mouse not administering the mastic oil (hereinafter, "control (mouse)" or "Control" in FIGS. 1 to 12 as stated below), a mouse administrating corn oil solution of 3% mastic oil (hereinafter, "mastic 3% (mouse)" or "Mastic 3%" in FIGS. 1 to 12 as stated below), and a mouse administrating corn oil solution of 30% mastic oil (hereinafter, "mastic 30% (mouse)" or "Mastic 30%" in FIGS. 1 to 12 as stated below) were prepared.

With regard to the respective allergic dermatitis model mice, an itch action observation after causing the hapten derivative allergy with TDI and an auricle thickness determination before the elicitation and after the elicitaition twenty four hours later.

First, with regard to the itch action observation, that is, an observation of a scratching (scratching off) behavior, we observed the scratching behavior for the auricular region and the dorsocervical in sixty minutes by recording records in sixty minutes about the respective allergic dermatitis model mice. A relationship a number of the scratching behavior and the respective mice is shown as a graph in FIG. 1.

From FIG. 1, in case comparing mastic 30% mouse and control mouse, a significant suppression of the scratching (scratching off) behavior was recognized regard to mastic 30% mouse. On the other hand, even if mastic 3% mouse was compared with control mouse, there was no change, on the contrary, the numbers of the scratching behavior was rather increased.

Next, with regard to the auricle thickness determination, the auricle thickness of the respective allergic dermatitis model mice was determined by using a vernier caliper before the elicitation of the hapten derivative allergy with TDI and after the elicitation of said allergy in twenty four hours. Those results are shown as FIG. 2.

From FIG. 2, with regard to control mouse, the auricle thickness was increased about 200 m in case comparing before the elicitation with after the elicitation in twenty four hours. In contrast with control mouse, the change of the auricle thickness was decreasing depending on the concentration of the mastic oil.

Next, with regard to the respective allergic dermatitis model mice (control mouse, mastic 3% mouse, mastic 30% mouse), analyzes of ear tissues were demonstrated on the basis of immunological test by extracting an auricle and an auricle lymph node of the respective mice after the scratching behavior observation and the auricle thickness determination and thus after euthanatizing the respective mice under isoflurane inhalation anesthetic.

First, the extracted auricle lymph node was grinded by using RPMI-1640 medium culture on cell strainer. With regard to the cell suspension obtained by grinding, total cell numbers were determined by Tali (trademark) image base cytometer, and the numbers ratio of the dendritic cell, helper T cell, and IgE positive B cell were determined by flow cytometer. These cell numbers are shown in FIG. 3 (dendritic cell number), FIG. 4 (helper T cell) and FIG. 5 (IgE positive B cell).

In FIG. 3, it was understood that the dendritic cell exhibiting antigen presentation was decreased by the administration of the mastic oil, the significant change was shown in both 3 and 30% concentrations, and the dendritic cell numbers were proportional to the high concentration.

In FIG. 4, the helper (naive) T cell receiving the antigen information from the dendritic cell increases an allergy reaction by performing class switch to Th2 type, however, the significant suppression of the number of the helper (naive) T cell was shown by the administration of the mastic oil.

In Th2 type allergy including atopic dermatitis, IgE plays a main role. Here, in FIG. 5, the significant suppression of the numbers of cells was seen in the numbers of B cell numbers producing IgE with administration of the mastic oil.

Next, the cell suspensions of the respective allergy dermatitis model mice were cultivated on 24~96 hours by using Dybabeads (trademark) Mouse T-Activator CD3/CD28 and, thereafter, the amount of the cytokine (IL-4, IL-9, IL-13) produced from T cell was determined by Enzyme Linked Immuno Sorbent Assay (ELISA). Further, IL-4 and IL-13 are produced from Th2 cell and perform B cell class switch to IgE production. On the other hand, IL-9 is produced by Th9 cell and is involved in propagations of blood megakaryocyte and mastocyte. The amounts of the respective cytokines are shown in FIG. 6 (IL-4), FIG. 7 (IL-9) and FIG. 8 (IL-13).

In FIG. 6, IL-4 increased with regard to mastic 3% mouse as compared to control mouse. On the other hand, with regard to mastic 30% mouse, the significant decreasing of IL-4 was shown.

In FIG. 7, IL-9 decreased with regard to both mastic 3% mouse and mastic 30% mouse as compared to control mouse depending on the concentration of the mastic oil.

In FIG. 8, the significant decreasing of IL-13 was shown with regard to both mastic 3% mouse and mastic 30% mouse as compared to control mouse depending on the concentration of the mastic oil.

Next, with regard to part of ear tissue (not ear lymph node), it was suspended in RPMI-1640 medium culture with using an electromotion homogenizer. After incubating it, supernatant was collected though centrifugal separation. With regard to the supernatant, total amounts of protein was determined, and EOTAXIN, IL-1β, and TSLP (thymic stromal lymphopoietin) were determined by ELISA. Further, the determined data was normalized by the total amounts of protein. Further, EOTAXIN is chemokine migrating an eosinophil, and the eosinophil is massively involved in an allergic aggravation. IL-1β and TSLP are involved in derivatives of a focal inflammatory reaction and Th2 type immunoreaction with producing keratinocyte. Changes of amounts of EOTAXIN, IL-1β, and TSLP are shown in FIG. 9 (EOTAXIN), FIG. 10 (IL-1β) and FIG. 11 (TSLP).

In FIG. 9, EOTAXIN increased with regard to mastic 3% mouse as compared to control mouse. On the other hand, with regard to mastic 30% mouse, the decreasing of EOTAXIN was shown.

In FIG. 10, IL-1β decreased with regard to both mastic 3% mouse and mastic 30% mouse as compared to control mouse depending on the concentration of the mastic oil.

In FIG. 11, TSLP increased with regard to mastic 3% mouse as compared to control mouse. On the other hand, with regard to mastic 30% mouse, the significant decreasing of TSLP was shown.

Next, total IgE amount in the blood serum (supernatant) is shown in FIG. 12. Although the mouse orally administrating the mastic oil is given recognition to the decreasing of total IgE amount, a concentration dependence of the mastic oil was not shown.

From the above results, with regard to the concentration of the mastic oil, 30% mastic oil may not be always realistically when considering, e.g., a practical application of the anti-allergy functional food composition of the present invention. However, the immunosuppressive effects of the cytokines contributing Th2 type allergy reaction were shown by orally administrating the mastic oil, therefore, a suggestion is obtained that it is possible to use mastic as the anti-allergy functional food composition.

[Example 2] Transdermal Administration Test of the Mastic Oil for Hapten Derivative Allergic Dermatitis Model Mice In the Example 2, the transdermal administration test was performed by using the hapten derivative allergic dermatitis model mice in order to test the effect of the mastic oil for Th2 type reaction generating from Th2 cell, which is the subgroup of the helper T cell inducing atopic dermatitis, as with the Example 1.

First, the hapten derivative allergic dermatitis mouse (hereinafter, "allergic dermatitis model mouse (mice)") used BALB/c SPF mouse (hereinafter, simply called "mouse") produced by Japan SLC Co, LtD. The allergic dermatitis model mouse was prepared by administering trilene-2,4-diisocyanate (TDI) as the hapten several times after domesticating the mouse on ten days receiving later. Further, abdominal hair of the mouse was removed before the day of first administration of TDI, moreover, TDI was administered on abdomen of the mouse again after removing the abdominal hair in three weeks from the first administration (sensitization). Furthermore, an elicitation of the mouse was caused by administering TDI to auricular region and dorsocervical of the mouse respectively in one week from the sensitization again. Further, in addition to the allergic dermatitis model mice, a non-handicapped mouse (hereinafter, "non-derivative (non-treatment) mouse" or "Untreated" in FIGS. 13 to 24), not derivating hapten, was prepared. Incidentally, the non-derivative mouse was used by domesticating the mouse on ten days receiving later as with the respective allergic dermatitis model mice.

Here, with regard to the administration of the mastic oil for the allergic dermatitis model mouse, the oil solving in tri (carpylic acid acid/capric acid) glyceryl was transdermally administered in about five weeks contiguously from the domestication start after the mouse arriving to the elicitation by administering TDI to auricular region and dorsocervical of the mouse respectively. Further, with regard to the allergic dermatitis model mice, three mice which are a mouse not administering the mastic oil (hereinafter, "control (mouse)" or "AD Control" in FIGS. 13 to 24 as stated below), a mouse administrating tri (carpylic acid acid/capric acid) glyceryl solution of 3% mastic oil (hereinafter, "mastic 3% (mouse)" or "Mastic 3%" in FIGS. 13 to 24 as stated below), and a mouse administrating tri (carpylic acid acid/capric acid) glyceryl solution of 5% mastic oil (hereinafter, "mastic 5% (mouse)" or "Mastic 5%" in FIGS. 13 to 24 as stated below) were prepared.

With regard to the respective allergic dermatitis model mice, an itch action observation after causing the hapten derivative allergy with TDI and a water transpiration in skin before the elicitation and after the elicitation twenty four hours later.

First, with regard to the itch action observation, that is, an observation of a scratching (scratching off) behavior, we observed the scratching behavior for the auricular region and the dorsocervical in sixty minutes by recording records in sixty minutes about the respective allergic dermatitis model mice in continuous five weeks.

The result is shown in FIG. 13.

From FIG. 13, with regard to the scratching (scratching off) behavior, in mastic 3% mouse and mastic 5% mouse, a significant suppression of the scratching (scratching off) behavior was recognized regard to mastic 5% mouse on 4~5 weeks but the number of the behavior was mostly constant until 3 weeks after the elicitation. On the other hand, with regard to control mouse, there was no change, on the contrary, the numbers of the scratching behavior was rather increased.

Next, also determination of the water transpiration in skin was determined before the elicitation and after the elicitation. The result was shown in FIG. 14.

From FIG. 14, with regard to control mouse, mastic 3% mouse, and mastic 5% mouse, the water transpirations of them were mostly same level in two weeks. However, the water transpiration of control mouse was continuously increasing after five weeks, in contrast, the suppression of the water transpiration in skin was seen in mastic 3% and 5% mouse.

Next, with regard to the respective allergic dermatitis model mice (non-derivative mouse, control mouse, mastic 3% mouse, mastic 5% mouse), analyzes of ear tissues were demonstrated on the basis of immunological test by extracting an auricle and an auricle lymph node of the respective mice after the scratching behavior observation and the auricle thickness determination and thus after euthanatizing the respective mice under isoflurane inhalation anesthetic.

First, the extracted auricle lymph node was grinded by using RPMI-1640 medium culture on cell strainer. With regard to the cell suspension obtained by grinding, total cell numbers were determined by Tali (trademark) image base cytometer, and the numbers ratio of the dendritic cell, helper T cell, and IgE positive B cell were determined by flow cytometer. These cell numbers are shown in FIG. 15 (dendritic cell number), FIG. 16 (helper T cell) and FIG. 17 (IgE positive B cell).

In FIG. 15, it was understood that the dendritic cell exhibiting antigen presentation was decreased by the administration of the mastic oil, the significant change was shown in both 3 and 5% concentrations, and the dendritic cell numbers were proportional to the high concentration.

In FIG. 16, the helper (naive) T cell receiving the antigen information from the dendritic cell increases an allergy reaction by performing class switch to Th2 type, however, the significant suppression of the number of the helper (naive) T cell was shown by the administration of the mastic oil.

In Th2 type allergy including atopic dermatitis, IgE plays a main role. Here, in FIG. 17, the significant suppression of the numbers of cells was seen in the numbers of B cell numbers producing IgE with administration of the mastic oil.

Next, the cell suspensions of the respective allergy dermatitis model mice were cultivated on 24~96 hours by using Dybabeads (trademark) Mouse T-Activator CD3/CD28 and, thereafter, the amount of the cytokine (IL-4, IL-9, IL-13) produced from T cell was determined by Enzyme Linked Immuno Sorbent Assay (ELISA). Further, IL-4 and IL-13 are produced from Th2 cell and perform B cell class switch to IgE production. On the other hand, IL-9 is produced by Th9 cell and is involved in propagations of blood megakaryocyte and mastocyte. The amounts of the respective cytokines are shown in FIG. 18 (IL-4), FIG. 19 (IL-9) and FIG. 20 (IL-13).

In FIG. 18, IL-4 decreased with regard to mastic 3% mouse as compared to control mouse. On the other hand, with regard to mastic 5% mouse, the significant decreasing of IL-4 was shown.

In FIG. 19, IL-9 decreased with regard to both mastic 3% mouse and mastic 5% mouse as compared to control mouse depending on the concentration of the mastic oil.

In FIG. 20, the significant decreasing of IL-13 was shown with regard to both mastic 3% mouse and mastic 5% mouse as compared to control mouse depending on the concentration of the mastic oil.

Next, with regard to part of ear tissue (not ear lymph node), it was suspended in RPMI-1640 medium culture with using an electromotion homogenizer. After incubating it, supernatant was collected though centrifugal separation. With regard to the supernatant, total amounts of protein was determined, and IL-1β, Periostin, and TSLP (thymic stromal lymphopoietin) were determined by ELISA. Further, the determined data was normalized by the total amounts of protein. Further, Periostin is one of extracellular matrix proteins. IL-1β and TSLP are involved in derivatives of a focal inflammatory reaction and Th2 type immunoreaction with producing keratinocyte. Changes of amounts of IL-1β, Periostin, and TSLP are shown in FIG. 21 (IL-1β), FIG. 22 (Periostin) and FIG. 23 (TSLP).

In FIG. 21, the significant decreasing of IL-1β was shown with regard to both mastic 3% mouse and mastic 30% mouse as compared to control mouse depending on the concentration of the mastic oil.

In FIG. 22, Periostin decreased with regard to both mastic 3% mouse and mastic 30% mouse as compared to control mouse depending on the concentration of the mastic oil.

In FIG. 23, TSLP increased with regard to mastic 5% mouse as compared to control mouse. On the other hand, with regard to mastic 3% mouse, the significant decreasing of TSLP was shown.

Next, the determined result of the number of controllability T cell in the lymph node is shown in FIG. 24. Although the mouse transdermally administrating the mastic oil was given recognition to the increasing of the number of controllability T cell, a concentration dependence of the mastic oil was not shown.

From the above results, the immunosuppressive effects of the cytokines contributing Th2 type allergy reaction were also shown by transdermally administrating the mastic oil, therefore, suggestions were obtained that it is possible to use mastic as the anti-allergy cosmetic or percutaneous external agent.

[Example 3] Effects of the Mastic Oil for IL-8 Discharged from Man Eosinophil and Acute Monocytic Leukemia Cells Next, for the purpose of investigating the effect of the mastic oil to cytokine (interleukin etc.), the effects of the mastic oil to a man eosinophil leukemia cell and an acute monocytic leukemia cell like a dendritic cell were considered by using a release of IL-8 as an index.

In Example 3, by each using THP-1 as the man acute monocytic leukemia cell and EoL-1 as the man eosinophil leukemia cell, the respective cells were cultivated at 37° C. under 5% carbon dioxide, thereafter, the respective cells and the mastic oil ($1.5 \times 10^{-8}$~$1.5 \times 10^{-3}$% concentration) were cultivated in 96 well plates on 24 hours and were further cultivated on 24 hours from adding LPS (Lipo Polysaccharide). After cultivating the respective cells and the mastic oil, a rate of cytokine (IL-8) was determined by ELISA. These results are shown in FIGS. 25 and 26.

FIG. 25 is a graph showing a suppression of an emission of IL-8 from the man acute monocytic leukemia cell (THP-1). From FIG. 25, an effect of a release suppression of IL-8 of the mastic oil to the man acute monocytic leukemia cell was not found to be without independent on the concentration of the mastic oil.

FIG. 26 is a graph showing a suppression of an emission of IL-8 from the eosinophilic leukemia cell (EoL-1). From FIG. 26, an effect of a release suppression of IL-8 of the mastic oil to the eosinophilic leukemia cell was found to be dependent on the concentration of the mastic oil.

In Example 3, the effect of the mastic oil to cytokine (IL-8) was considered by using two leukemia cells. There seems to be plenty of room for consideration, at least, the suggest result was obtained that the mastic oil has the immunosuppressive effect for cytokine etc contributing the allergy reaction of man.

[Example 4] Preparation of the Anti-Allergy Functional Food Composition

On the basis of the above Example 1, the anti-allergy functional food composition was prepared. The blending example is as below Table 1.

TABLE 1

| Blending amount of the anti-allergy functional food composition | |
|---|---|
| Mastic powder | 5.0% |
| Mastic essential oil | 1.0% |
| Sorbitol | 40.0% |
| Erythritol | 10.0% |
| Xylitol | 5.0% |
| Chitosan | 2.0% |
| Papain | 2.0% |
| Aromatic | 2.0% |
| Sweetener | 2.00% |
| Crystal Cellrose | 26.0% |
| Calcium stearate | 3.00% |
| Citric acid | 2.0% |
| | 100% |

Incidentally, the anti-allergy functional food composition of Example 4 was prepared by kneading according to routine method. Further, the preparation of the food composition is not only routine method, but also general preparation method. Even if taking the various preparation methods, with regard to the above the suppression of the allergy reaction, we add and declare that there is not much difference between the results of Example 1 and the results.

[Example 5] Preparation of the Anti-Allergy Percutaneous External Agent (Cosmetic)

On the basis of the above Example 2, the anti-allergy percutaneous external agent (cosmetic) was prepared. The blending example is as below Table 2.

TABLE 2

| Blending amount of the anti-allergy percutaneous external agent (cosmetic) | |
|---|---|
| Mastic oil | 30.0% |
| Vaserine | 70.0% |
| | 100% |

Incidentally, the anti-allergy percutaneous external agent (cosmetic) of Example 5 was prepared by kneading according to routine method. Further, the preparation of the agent is not only routine method, but also general preparation method. Even if taking the various preparation methods, with regard to the above the suppression of the allergy reaction, we add and declare that there is not much difference between the results of Example 2 and the results.

INDUSTRIAL APPLICABILITY OF THE PRESENT INVENTION

In the above embodiments and Examples, although we explain about the anti-allergy functional food composition, cosmetic and percutaneous external agent of the present invention, it is possible to apply as the anti-allergy medicament for man, dog or cat because of using the mastic oil in the present invention.

The invention claimed is:

1. An anti-allergy cosmetic comprising an anti-allergy functional food composition containing a mastic component as an immunosuppressive participating component,
    wherein the anti-allergy cosmetic comprises the mastic component and a humectant, and
    wherein the mastic component is a mastic resin.

2. The anti-allergy cosmetic according to claim 1, wherein the mastic resin is a mastic oil made by dissolving a diluent and the mastic resin, the mastic oil is a solution, and the concentration of the mastic resin in the solution is 0.1-60 weight %.

3. The anti-allergy cosmetic according to claim 2, wherein the diluent is at least one selected from the group consisting of polyhydric alcohol fatty acid ester, alcohol solvent, mineral oil and vegetable oil.

4. The anti-allergy cosmetic according to claim 2, wherein the anti-allergy functional food composition comprises 0.01-80% of a blending amount of the mastic oil based on the total amount of the composition.

5. The anti-allergy cosmetic according to claim 1, wherein an immunosuppressive target allergy is I type or IV type in Coombs classification.

6. A method of treating an allergy, comprising administering a therapeutically effective amount of the anti-allergy cosmetic according to claim 1 to a subject in need thereof.

7. The method according to claim 6, wherein the method targets an immunosuppressive target allergy type I or an immunosuppressive target allergy type IV in Coombs classification.

* * * * *